US00PP19551P2

(12) United States Plant Patent
Zary

(10) Patent No.: US PP19,551 P2
(45) Date of Patent: Dec. 9, 2008

(54) FLORIBUNDA ROSE PLANT NAMED 'JACORBET'

(50) Latin Name: *Rosa hybrida*
Varietal Denomination: JACorbet

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,354

(22) Filed: Nov. 28, 2007

(51) Int. Cl.
*A01H 5/00* (2006.01)

(52) U.S. Cl. ..... Plt./146

(58) Field of Classification Search ..... Plt./146
See application file for complete search history.

*Primary Examiner*—Kent L. Bell
*Assistant Examiner*—Georgia Helmer
(74) *Attorney, Agent, or Firm*—Klarquist Sparkman, LLP

(57) ABSTRACT

Floribunda rose plant having flowers with a very novel flower color; a profusion of thorns; a compact, well-branched plant structure; large, pyramidal clusters of flowers; and dark green, glossy foliage.

1 Drawing Sheet

Genus and species: *Rosa hybrida.*
Variety denomination: 'JACorbet'.

ORIGIN OF THE INVENTION

The present invention relates to a new and distinct variety of a floribunda rose plant named 'JACorbet' which was originated by me by crossing the variety 'JACzotta' (U.S. Plant Pat. No. 12,128, seed parent), with the variety 'JACzap' (U.S. Plant Pat. No. 12,073, pollen parent).

BACKGROUND OF THE INVENTION

The primary objective of this breeding was to produce a new floribunda rose variety having the two-tone color pattern of the 'JACzotta' combined with the color of the male parent 'JACzap'.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very novel flower color.
2. Profusion of thorns.
3. Compact, well-branched plant.
4. Large, pyramidal clusters of flowers.
5. Dark green, glossy foliage.

Asexual reproduction of this new variety by budding on Dr. Huey understock (not patented), as performed at Wasco, Calif., shows that the foregoing characteristics and distinctions come true to form and are established and transmitted through succeeding propagations.

Comparison with Parents

'JACorbet' differs from 'JACzotta' in flower color. 'JACorbet' has flowers that are a smokey orange color while 'JACzotta' has flowers that are a raspberry pink color. 'JACorbet' differs from 'JACzap' in flower color. 'JACzap' has flowers that are a yellow-orange color. 'JACorbet' differs from both parents in thorniness.

Comparison with Similar Variety

The closest variety is believed to be 'WEKpaltlez' (U.S. Plant Pat. No. 15,155). 'JACorbet' differs from 'WEKpaltlez' in thorniness ('JACcorbet' is much more thorny than 'WEKpaltlez'). 'JACcorbet' is also much more compact than 'WEKpaltlez'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'JACzotta' (U.S. Plant Pat. No. 12,128).
*Pollen parent.*—'JACzap' (U.S. Plant Pat. No. 12,073).

FLOWER

Observations were made from January 2005 to October 2007 of plants that were two to three years old at the completion of observation. These observed plants were growing in a garden environment at Somis, Calif.

Blooming habit: Continuous.
Bud:
*Size.*—About 20 mm long and 16 mm in diameter when the petals start to unfurl.
*Form.*—The bud form is long, pointed ovoid.

*Color.*—When sepals first divide, bud color is Orange-Red Group 34A. When half blown, the upper sides of the petals are Orange-Red Group 34B and the lower sides of the petals are Orange-Red Group 34C on about the outer two-thirds of the petal and Yellow-Orange Group 15C on about the inner one-third of the petal.

*Sepals.*—Color: Upper surface: Green Group 138B. Lower surface: Yellow-Green Group 146B but if exposed to bright sun will have an overcast of Greyed-Red Group 178A. Length: 25 mm. Width: 9 mm. Shape: Subulate. Surface: Hoary. There are three lightly appendaged sepals. There are two unappendaged sepals with hairy edges.

*Receptacle.*—Color: Yellow-Green Group 146B. Shape: Apple. Size: Medium, about 6 mm long×6 mm in width. Surface: Smooth.

*Peduncle.*—Length: Short, averaging about 35 mm. Surface: Smooth with an occasional gland. Color: Yellow-Green Group 146D. Strength: Stiff, erect.

Bloom:

*Size.*—Medium. Average open diameter is about 80–90 mm.

*Borne.*—Several together in clusters of 3–11 blooms having pyramidal shape.

*Stems.*—Strength: Strong. Average length is about 30–40 cm with a diameter of 6–7 mm.

*Form.*—When first open: High centered. Permanence: Flattens with age, all petals curl.

*Petalage.*—Number of petals under normal conditions: 20–25.

*Color.*—The upper sides of the petals are Orange-Red Group 34B. The reverse sides of the petals are Orange-Red Group 34C on about the outer two-thirds of the petal surface and Yellow-Orange Group 15C on about the inner one-third of the petal surface. The base of the petals has a distinct color spot, about 7 mm×7 mm, of Yellow Group 9A. The major color on the upper sides is Orange-Red Group 34B.

*Variegations.*—Occasionally, there is a Yellow Group 9A stripe along the midrib of interior petals.

*Discoloration.*—The general tonality at the end of the first day: No change. At the end of the third day: A gradual change to Orange-Red Group N34D.

*Fragrance.*—Moderate, fruity.

Petals:

*Surface texture.*—Smooth, leathery.

*Shape.*—Obdetoid to obcordate.

*Margin.*—Entire.

*Apex shape.*—Obcordate.

*Base shape.*—Rounded.

*Form.*—Tips slightly recurved.

*Arrangement.*—Imbricated.

*Petaloids.*—Number: Few, from 0 to 3. Size: 5–20 mm length and 3–10 mm wide. Color like the petals.

*Persistence.*—Petals drop off cleanly before drying.

*Lastingness.*—On the plant: Short (about 3–5 days). As a cut flower: Short (about 4–6 days).

Reproductive parts:

*Stamens.*—Number: 80–90. Length: 8–9 mm. Anthers: Length: 2–3 mm. Color: Yellow-Orange Group 22C. Arrangement: Regular around styles. Filaments: Color: Red Group 45D. Length: 7–8 mm. Pollen: Color: Greyed-Orange Group 167D.

*Pistils.*—Number: 40–45. Length: 6–7 mm. Styles: Color: Red Group 46B. Length: 5–6 mm. Stigmas: Color: Yellow-Orange Group 15D. Length: 1 mm.

*Hips.*—None observed. Has not set seed in controlled crosses but does produce viable pollen.

PLANT

*Form.*—Bush.

*Growth.*—Vigorous, upright, branching, compact.

*Age to maturity.*—Two years.

*Mature plant.*—Height: 80–90 cm. Width: 60–70 cm.

*Rootstock.*—Dr. Huey (not patented).

Foliage: Number of leaflets on normal mid-stem leaves: 5.

*Size.*—Medium. About 12 cm long×8 cm wide.

*Quantity.*—Abundant.

*Color.*—New foliage: Upper side: Greyed-Red Group 178A. Lower side: Greyed-Red Group 178B. Old foliage: Upper side: Green Group 136A. Lower side: Green Group 137B.

Leaflets:

*Size.*—About 55 mm long×35 mm wide.

*Shape.*—Pointed oval.

*Base shape.*—Rounded.

*Apex shape.*—Aristulate.

*Texture.*—Glossy, smooth.

*Edge.*—Serrated.

*Serrations.*—Single.

*Petiole.*—Color: Green Group 138B.

*Petiole rachis.*—Color: Green Group 138B. Underside: Smooth with prickles and glands.

*Auricles.*—None observed.

*Stipules.*—Length: 20–22 mm, serrated.

*Disease resistance.*—Resistant to rust and mildew, susceptible to blackspot under normal growing conditions.

*Pest resistance.*—None observed.

*Vein color.*—Green Group 138B.

*Venation pattern.*—Reticulate.

Wood:

*New wood.*—Color: Yellow-Green Group 146B. Bark: Smooth.

*Old wood.*—Color: Yellow-Green Group 146A. Bark: Smooth.

Prickles:

*Quantity.*—Ordinary, on main canes from base: 9–15 per 15 cm of wood. Many, on laterals from main canes: 25–30 per 15 cm of wood.

*Form.*—Straight or very slightly hooked down.

*Length.*—8–10 mm.

*Color when young.*—Greyed-Red Group 178B.

*Color when mature.*—Greyed-Orange Group 177B.

Small prickles:

*Quantity.*—On main stalks: Many, 180–220 per 15 cm stem. On laterals: Few, 10–20 per 15 cm of lateral cane.

*Color.*—Same as large prickles.

Winter hardiness: Hardy to Zone 5.

I claim:

1. A new and distinct variety of floribunda rose plant, substantially as herein shown and described, characterized particularly by a very novel flower color; profusion of thorns; compact, well-branched plant; large, pyramidal clusters of flowers; and dark green, glossy foliage.

* * * * *

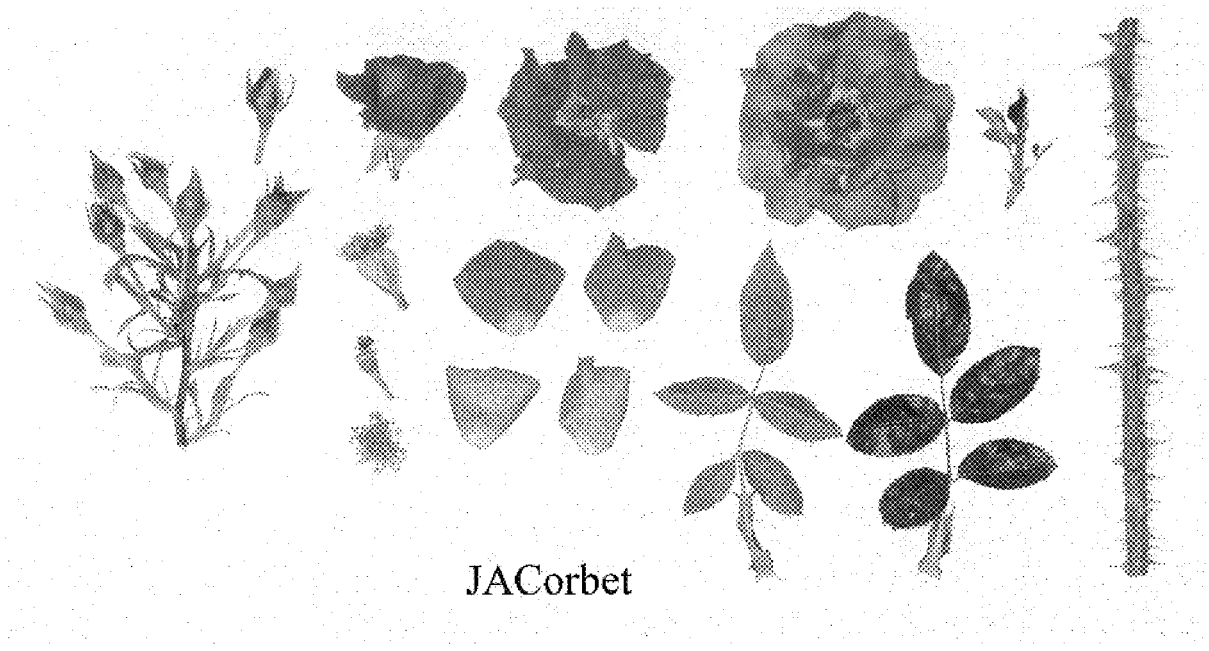
JACorbet